United States Patent
Mooney et al.

(10) Patent No.: US 6,714,667 B1
(45) Date of Patent: Mar. 30, 2004

(54) USER INTERFACE FOR IMAGING SYSTEM

(75) Inventors: Matthew Mooney, Westford, MA (US); Patrick G Rafter, Windham, NH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 684 days.

(21) Appl. No.: 09/616,340

(22) Filed: Jul. 14, 2000

(51) Int. Cl.$^7$ .................................................. G06K 9/00
(52) U.S. Cl. ...................................................... 382/128
(58) Field of Search ........................ 382/128; 348/163; 600/407, 434, 443, 444, 446, 448; 73/1.82, 579, 646, 647, 703, 611; 367/155, 180; 700/280

(56) References Cited

U.S. PATENT DOCUMENTS

| | | | |
|---|---|---|---|
| 4,368,410 A | * 1/1983 | Hance et al. | 318/116 |
| 4,819,621 A | * 4/1989 | Ueberle et al. | 601/4 |
| 5,472,405 A | * 12/1995 | Buchholtz et al. | 601/2 |
| 6,159,153 A | * 12/2000 | Dubberstein et al. | 600/443 |
| 6,413,218 B1 | * 7/2002 | Allison et al. | 600/443 |
| 6,423,007 B2 | * 7/2002 | Lizzi et al. | 600/458 |
| 6,436,045 B1 | * 8/2002 | Rafter et al. | 600/447 |
| 6,575,956 B1 | * 6/2003 | Brisken et al. | 604/500 |
| 2001/0021371 A1 | * 9/2001 | Eriksen et al. | 424/9.52 |
| 2001/0051131 A1 | * 12/2001 | Unger | 424/9.5 |
| 2002/0151777 A1 | * 10/2002 | Hynynen et al. | 600/407 |

* cited by examiner

*Primary Examiner*—Andrew W. Johns
*Assistant Examiner*—Shervin Nakhjavan
(74) *Attorney, Agent, or Firm*—John Vodopia (57) ABSTRACT

A user interface for an imaging device provides a first controller for adjusting the output of a transducer and a second controller for high power imaging. A control circuit, in response to input from the first controller adjusts the output power level of the imaging device and when a power level over a predetermined value is requested requires input from the second controller prior to adjusting the output of the imaging device to the requested power level. Alternatively, the first control can be used to set the imaging device for low power imaging, while the second control is used to set the imaging device for high power imaging. The imaging device can also be provided with a variety of display interfaces to facility safe high power imaging. A graph of power vs. depth may be displayed in conjunction with the ultrasound image and the portions of the image that receive the highest power can be highlighted.

17 Claims, 7 Drawing Sheets

USER INTERFACE FOR IMAGING SYSTEM

BACKGROUND OF THE INVENTION

The present invention relates to methods and apparatus providing a user interface that reduces or eliminates safety concerns with high power imaging, and, in particular, serve to provide mechanical, visual and audible feedback during high MI imaging on a ultrasound system.

Ultrasound imaging involves using a transducer, generally comprising mechanical/electric converters, such as piezoelectric elements, to transmit ultrasound waves into a subject and receive the echoes thereof. During transmit, the piezoelectric elements are excited with an electrical signal to vibrate at a selected frequency thereby generating an ultrasound signal. By selectively exciting the individual elements, the ultrasound signal can be steered and focused. During receive, the piezoelectric elements are excited by the returning echoes and, in turn, output electrical signals that can be processed to create an image of the insides of the subject.

Much of the current innovation in medical ultrasound diagnostic equipment and procedures focuses on harmonic imaging. It has been found that tissue structures within a body produce echoes at a harmonic of the frequency of the impinging signal ("harmonic echoes"). In harmonic imaging, a signal of a fundamental frequency is transmitted by a transducer into a patient and an image is constructed using the echoes from the patient exhibiting a harmonic frequency of the fundamental frequency. The harmonic echoes, while being more accurate of the structure being imaged, are significantly weaker than echoes exhibiting the fundamental frequency. This presents challenges in designing harmonic imaging systems.

One method of improving harmonic imaging involves the sequential transmission of waveforms with alternating polarities. Upon receive, the echoes resulting from the alternating waveforms are combined so as to eliminate parts of echoes exhibiting the fundamental frequency. Using this methods, it has been claimed, the harmonic content can be increased as much as 6 dB. One example of such a method is described in U.S. Pat. No. 5,833,613 to Averkou et al.

A method to improve harmonic imaging using arbitrary wave functions, is currently under investigation. Standard ultrasound transducers are excited by pulse generator driver circuits which generate rectangular waveforms. When excited in this manner, transducers emit signals, which show up as noise, exhibiting a frequency that is a harmonic of the desired frequency along with the desired signal. The use of a so-called arbitrary wave functions has been explored as a means to lower the amount of noise (and especially the transmitted harmonic noise) output by a transducer. Arbitrary wave function driver circuits output a shaped excitation waveform, typically using Gaussian or Hamming modulation. At least one manufacture claims to suppress the transmitted second harmonic frequencies by 30 dB using arbitrary waveforms. Example of such a method are described in U.S. Pat. No. 5,675,554 to Cole et al. and U.S. Pat. No. 5,740,128 to Hossack et al.

Unfortunately, both of the above-described techniques require complex and expensive hardware to implement. Further, only the first method (the sequential transmission of waveforms with alternating polarities) actually enhances the second harmonic, but only by about 6 dB. The first technique is also subject to motion artifacts. Finally, both methods are limited by the noise floor inherent in any ultrasound system.

The present inventors believe that future improvements in ultrasound imaging, including harmonic imaging, require the use of high pressure transmit waveforms. In general, more contrast is obtained with increased ultrasound pressures. Tissue generates second harmonic pressure proportional to a function of the pressure of the transmitted fundamental frequency, distance, and frequency of the fundamental frequency.

$P_2 = f(P_1^2, z, f, \ldots)$   Where $P_2$ = pressure of second harmonic
$P_1$ = pressure of transmitted fundamental frequency
$z$ = distance
$f$ = frequency of fundamental frequency Due to current limitations in transducer design, specifically a lack of bandwidth, most harmonic imaging systems only monitor the second harmonic of the fundamental frequency of the transmit signal. In the future, technologies such as single crystal transducers will provide significant increases in bandwidth, making it possible to monitor the second, third and possibly even the fourth harmonic with a single transducer, assuming the transmit waveform has enough power to generate such higher order harmonics. It is hoped that constructing an image using the higher harmonics will provided even more contrast for even clearer images. Generally speaking the pressure of the $n^{th}$ order harmonic is proportional to $P_1^n$. This relationship requires the use of higher fundamental pressures so as to yield higher harmonic pressures.

Unfortunately, current limitations imposed by the U.S. Federal Drug Administration (the FDA) limit the output of medical ultrasound transducers to 1.9 MI.

$MI = P/f^{1/2}.$

The 1.9 MI limitation is based mostly on safety concerns that have not been proven in vivo. Nevertheless, if high MI ultrasound devices are to become reality, the supposed safety concerns will have to be addressed in a positive pro-active manner.

Accordingly, the present Inventors have recognized a need for methods and apparatus for reducing safety concerns with high MI imaging, and, in particular, have realized a new an improved user interface providing feedback and warnings during high MI imaging.

SUMMARY OF THE INVENTION

A user interface for providing increased safety when driving a transducer of an ultrasound imaging device at high MIs. An ultrasound imaging device is provided with a first controller for adjusting the output of a transducer and a second controller for high MI imaging. A control circuit, in response to input from the first controller adjusts the output power level of the transducer and when a power level over a predetermined value is requested, requires input from the second controller prior to adjusting the output of the transducer to the requested power level. Alternatively, the first control can be used to set the transducer for low MI imaging, while the second control sets the transducer for high MI imaging. The ultrasound imaging system can also be provided with a variety of display modes to facility safe high MI imaging. For example, a graph of MI vs. depth can be displayed in conjunction with the ultrasound image and/or the portions of the image that receive the highest MI can be highlighted.

BRIEF DESCRIPTION OF THE DRAWINGS

These and other objects and advantages of the invention will become apparent and more readily appreciated from the following description of the preferred embodiments, taken in conjunction with the accompanying drawings of which.

DESCRIPTION OF THE PREFERRED EMBODIMENTS

Reference will now be made in detail to the present preferred embodiments of the present invention, examples of which are illustrated in the accompanying drawings, wherein like reference numerals refer to like elements throughout.

The detailed description which follows is presented in terms of routines and symbolic representations of operations of data bits within a memory, associated processors, and possibly networks, and network devices. These descriptions and representations are the means used by those skilled in the art effectively convey the substance of their work to others skilled in the art. A routine is here, and generally, conceived to be a self-consistent sequence of steps or actions leading to a desired result. Thus, the term "routine" is generally used to refer to a series of operations performed by a processor, be it a central processing unit of an ultrasound system, or a secondary processing unit of such an ultrasound system, and as such, encompasses such terms of art as "program," "objects," "functions," "subroutines," and "procedures." Accordingly, a "routine" is a method practiced on or in conjunction with at least one physical memory and associated processor.

In general, the sequence of steps in the routines require physical manipulation of physical quantities. Usually, though not necessarily, these quantities take the form of electrical or magnetic signals capable of being stored, transferred, combined, compared or otherwise manipulated. Those of ordinary skill in the art conveniently refer to these signals as "bits", "values", "elements", "symbols", "characters", "images", "terms", "numbers", or the like. It should be recognized that these and similar terms are to be associated with the appropriate physical quantities and are merely convenient labels applied to these quantities.

In the present case, the routines and operations are machine operations to be performed in conjunction with human operators. Useful machines for performing the operations of the present invention include the Agilent Technologies SONOS 5500 and other similar devices. In general, the present invention relates to routines, including method steps, and software, along with associated hardware including computer readable medium, configured to store and/or process electrical or other physical signals to generate other desired physical signals.

The apparatus set forth in the present application is preferably specifically constructed for the required purpose, i.e. ultrasound imaging, but the methods recited herein may operate on a general purpose computer or other network device selectively activated or reconfigured by a routine stored in the computer and interface with the necessary ultrasound imaging equipment. The procedures presented herein are not inherently related to any particular ultrasonic system, computer or other apparatus. In particular, various machines may be used with routines in accordance with the teachings herein, or it may prove more convenient to construct a more specialized apparatus to perform the required steps. In certain circumstances, when it is desirable that a piece of hardware possess certain characteristics, these characteristics are described more fully in the following text. The required structures for a variety of these machines may appear in the description given below. Machines which may perform the functions of the present invention include those manufactured by such companies as AGILENT TECHNOLOGIES, and ADVANCED TECHNOLOGY LABORATORIES, INC., as well as other manufacturers of ultrasound equipment.

With respect to the software described herein, those of ordinary skill in the art will recognize that there exists a variety of platforms and languages for creating software for performing the procedures outlined herein. Those of ordinary skill in the art also recognize that the choice of the exact platform and language is often dictated by the specifics of the actual system constructed, such that what may work for one type of system may not be efficient on another system.

Figure 1:
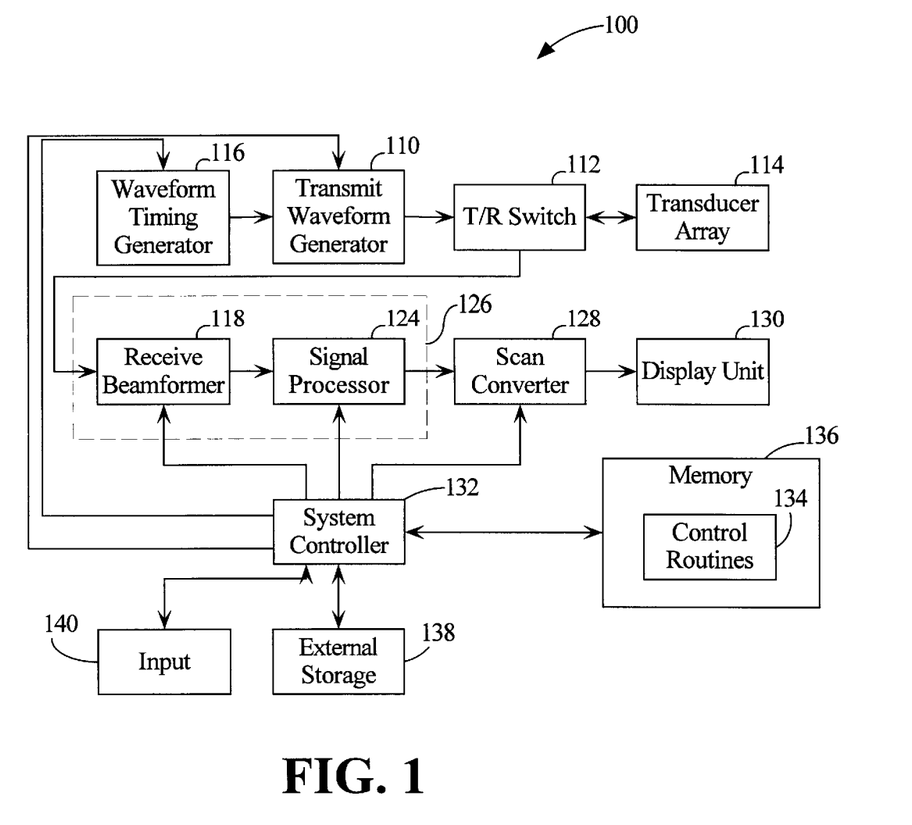
FIG. 1 is a block diagram of an ultrasound imaging system for use with preferred embodiments of the present invention.

FIG. 1 is a block diagram of an ultrasound imaging system 100 for use with preferred embodiments of the present invention. It will be appreciated by those of ordinary skill in the relevant arts that the ultrasound imaging system 100, as illustrated in FIG. 1, and the operation thereof as described hereinafter is intended to be generally representative of such systems and that any given system may differ significantly from that shown in FIG. 1, particularly in the details of construction and operation of such system. As such, the ultrasound imaging system 100 is to be regarded as illustrative and exemplary and not limiting as regards the invention described herein or the claims attached hereto.

The ultrasound imaging system shown in FIG. 1 is shown as configured for the use of arbitrary wave functions, but could be equally configured for standard pulse operation. A transmit waveform generator 110 is coupled through a transmit/receive (T/R) switch 112 to a transducer array 114, which includes an array of transducer elements. The T/R switch 112 typically has one switch element for each transducer element. The transmit waveform generator 110 receives waveform timing sequences from a waveform timing generator 116. In the case of a pulsed system the transmit waveform generator 110 is replaced with a transmit beamformer and the waveform timing generator 116 is replaced with a pulse generator. The transducer array 114, energized by the transmit waveform generator 110, transmits ultrasound energy into a region of interest (ROI) in a patient's body and receives reflected ultrasound energy, or echoes, from various structures and organs within the patient's body. As is known in the art, by appropriately delaying the waveforms applied to each transducer element by the transmit waveform generator 110, a focused ultrasound beam is transmitted.

The transducer array 114 is also coupled, through the T/R switch 112, to a receive beamformer 118. Ultrasound energy from a given point within the patient's body is received by the transducer elements at different times. The transducer elements convert the received ultrasound energy to transducer signals which may be amplified, individually delayed and then summed by the receive beamformer 118 to provide a beamformer signal that represents the received ultrasound level along a desired receive line. The receive beamformer 18 may be a digital beamformer including an analog-to-digital converter for converting the transducer signals to digital values. As known in the art, the delays applied to the transducer signals may be varied during reception of ultrasound energy to effect dynamic focusing. The process is repeated for multiple scan lines to provide signals for generating an image of the region of interest in the patient's body. The receive beamformer 118 may, for example, be a digital beamformer of the type used in the AGILENT SONOS 5500 ultrasound system manufactured and sold by AGILENT TECHNOLOGIES.

The scan pattern may be a sector scan, wherein scan lines typically originate at the center of the transducer array 114 and are directed at different angles. Linear, curvilinear and other scan patterns may also be utilized. Furthermore, the scan pattern may be two-dimensional or three-dimensional. In an alternative system configuration, different transducer elements are used for transmitting and receiving. In that configuration, the T/R switch 112 is not required, and the transmit waveform generator 110 and the receive beamformer 118 are connected directly to the respective transmit and receive transducer elements.

The beamformer signals are applied to a signal processor 124 which processes the beamformer signal for improved image quality and may include processes such as harmonic processing. The receive beam former 118 and the signal processor 124 constitute an ultrasound receiver 126. The output of the signal processor 124 is supplied to a scan converter 128 which converts sector scan or other scan pattern signals to conventional raster scan display signals. The output of the scan converter 128 is supplied to a display unit 130, which displays an image of the region of interest in the patient's body. In the case of a three-dimensional scan pattern, the scan converter 118 may be replaced by an image data buffer that stores the three-dimensional data set and a processor that converts the three-dimensional data set to a desired two-dimensional image.

A system controller 132 provides overall control of the system. The system controller 132 performs timing and control functions and typically includes a microprocessor operating under the control of control routines 134, stored in a memory 138. As will be discussed in detail below, the control routines 134 include a variety of routines to ensure the safe use of high MI ultrasound scanning. The system controller 132 also utilizes a memory 136 to store intermediate values, including system variables describing the operation of the ultrasound imaging system 100. External storage 138 may be utilized for more permanent and/or transportable storage of data. Examples of devices suitable for use as the suitable external storage 138 include a floppy disk drive, a CD-ROM drive, a videotape unit, etc.

An input unit 140 provides an operator interface using a combination of input devices, such as keys, sliders, switches, touch screens and track balls.

Figure 2:
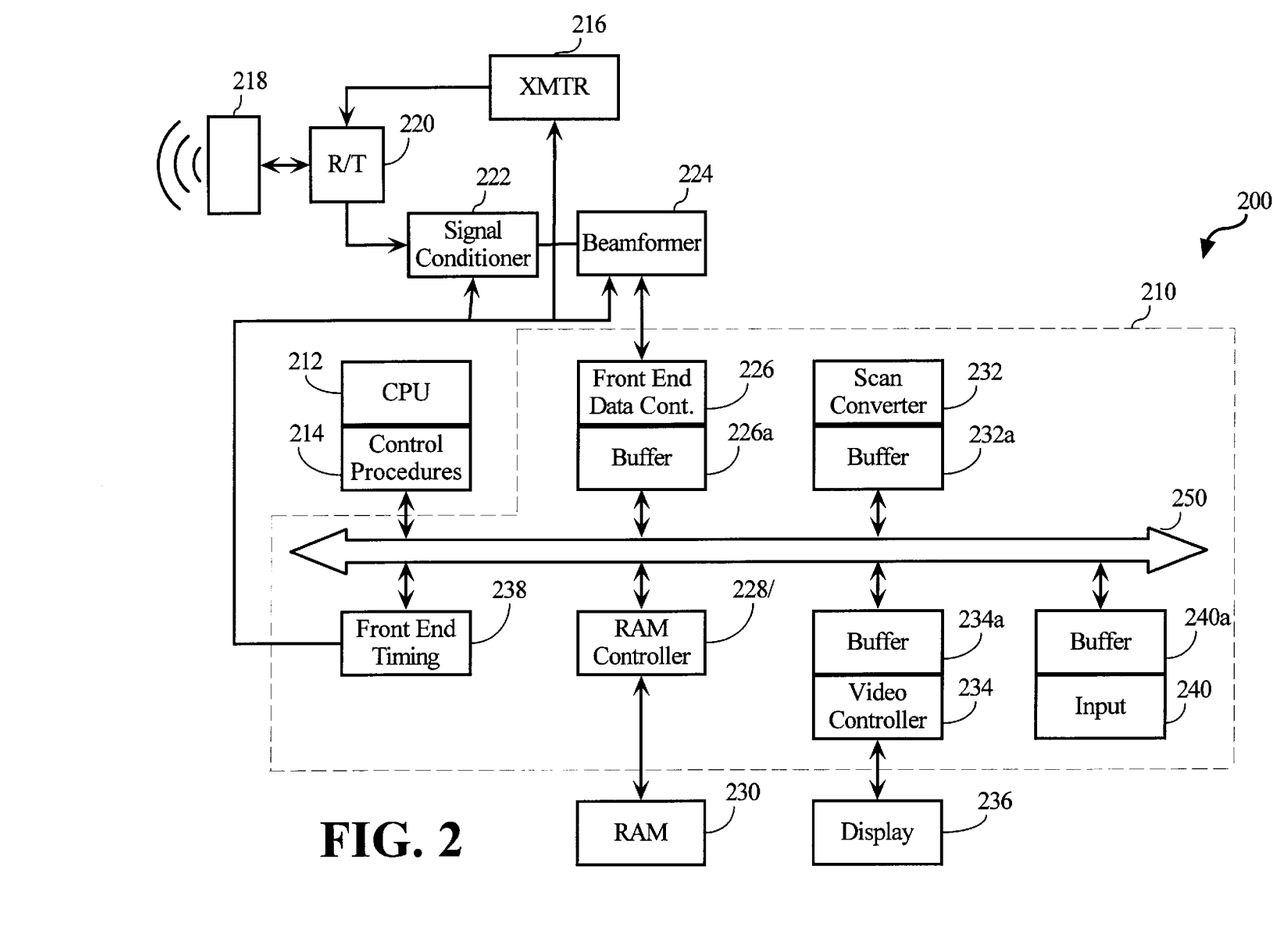
FIG. 2 is a block diagram of an alternative ultrasound imaging system for use with preferred embodiments of the present invention.

FIG. 2 is a block diagram of an alternative ultrasound imaging system 200 for use with preferred embodiments of the present invention. It will be appreciated by those of ordinary skill in the relevant arts that the ultrasound imaging system 200, as illustrated in FIG. 2, and the operation thereof as described hereinafter is intended to be generally representative such systems and that any particular system may differ significantly from that shown in FIG. 2, particularly in the details of construction and operation of such system. As such, the ultrasound imaging system 200 is to be regarded as illustrative and exemplary and not limiting as regards the invention described herein or the claims attached hereto.

The ultrasound imaging system shown in FIG. 2 is configured for the use of pulse generator circuits, but could be equally configured for arbitrary waveform operation. In contrast to the ultrasound system 100, shown in FIG. 1, the ultrasound system 200 utilizes a centralized bus architecture more suitable for the incorporation of standard personal computer ("PC") type components.

The ultrasound system 200 includes a transducer 218 which, in the known manner, scans an ultrasound beam, based on a signal from a transmitter 216, through an angle. Backscattered signals, i.e. echoes, are sensed by the transducer 218 and are fed through a received/transmit switch 220 to a signal conditioner 222 and, in turn, to a beamformer 224. The signal conditioner 222 receives the backscattered ultrasound analog signals and conditions those signals by amplification and forming circuitry prior to their being fed to the beamformer 224. Within the beamformer 224, the ultrasound signals are converted to digital values and are configured into "lines" of digital data values in accordance with amplitudes of the backscattered signals from points along an azimuth of the ultrasound beam.

The beamformer 224 feeds the digital values to an application specific integrated circuit (ASIC) 210 which incorporates the principal processing modules required to convert the digital values into a form more conducive to video display data for feed to a display 236.

A front end data controller 226, receives the lines of digital data values from the beamformer 224 and buffers each line, as received, in an area of a buffer 226a. After accumulating a line of digital data values, the front end data controller 226 dispatches an interrupt signal, via a bus 250, to a shared central processing unit (CPU) 212. The CPU 212 executes control procedures 214 including procedures that are operative to enable individual, asynchronous operation of each of the processing modules within the ASIC 210. More particularly, upon receiving the interrupt signal, the CPU 212 causes a line of digital data values data residing in the buffer 226a to be fed to a random access memory (RAM) controller 228 for storage in a random access memory (RAM) 230 which constitutes a unified, shared memory. RAM 230 stores instructions and data for the CPU 212, lines of RF digital data values and data being transferred between individual modules in the ASIC 230, all under control of the RAM controller 228.

A front end timing controller 238 is controlled by one of the control procedures 214 to output timing signals to the transmitter 216, the signal conditioner 222 and the beam former 224 so as to synchronize their operations with the operations of the modules within ASIC 210. The front end timing controller 238 further issues timing signals which control the operation of the bus 250 and various other functions within the ASIC 210.

As aforesaid, the control procedures 214 operates the CPU 212 to enable the front end data controller 226 to move the lines of digital data values into the RAM controller 228 where they are then stored in RAM 230. Since the CPU 212 controls the transfer of lines of digital data values, it senses when an entire image frame has been stored in RAM 230. At this point, the CPU 212, in conjunction with the control procedures 214, recognizes that data is now available for operation by the scan converter 232, at which point, the CPU 212 notifies the scan converter 232 that it can access the frame of data from RAM 230 for processing.

To access the data in RAM 230 (via RAM controller 228), the scan converter 232 interrupts the CPU 212 to request a line of the data frame from RAM 230. Such data is then transferred to a buffer 232a of the scan converter 232, and is processed to put it into a displayable form. This process is repeated for each subsequent line of digital data values of the image frame from RAM 230. The resulting processed data is fed, via the RAM controller 228, into RAM 230 as video-ready data. The CPU 212 and the control procedures 214, via the interrupt procedure described above, sense the completion of the operation of the scan converter 232. The video controller 234, on a continuing basis, interrupts the CPU 212 which responds by causing a feed of lines of video data thereto from RAM 230 into a buffer 234a of the video controller 234 for display by the display monitor 236.

An input unit 240 provides an operator interface using a combination of input devices, such as keys, sliders, switches, touch screens and track balls, via a buffer 240a.

Figure 3:
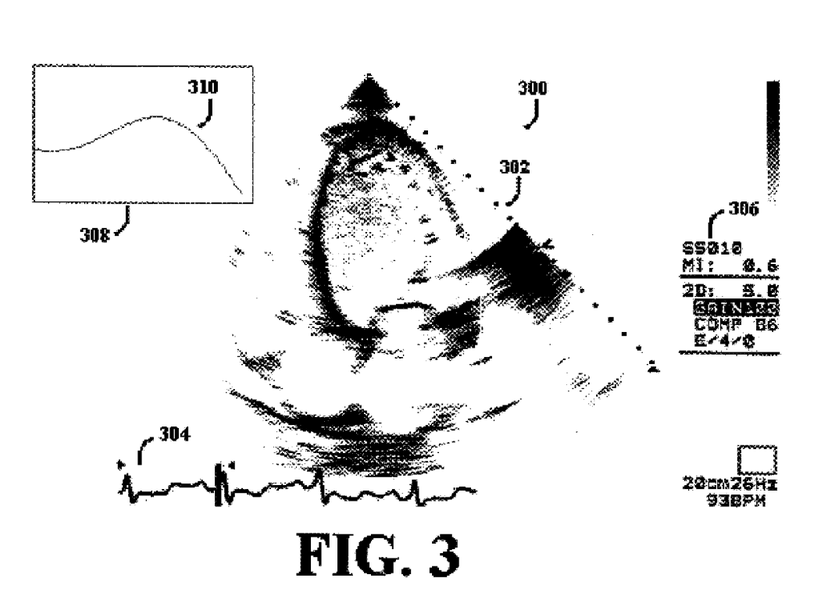
FIG. 3 is a screen shot of an image produced by an ultrasound system in accordance with a first preferred embodiment of the present invention.

FIG. 3 is a screen shot of an image 300 produced by an ultrasound system in accordance with a first preferred embodiment of the present invention. In general the image 300 is divided into four (4) zones. The primary zone 302 shows the image obtained by processing echo signals received by a transducer. In this case an apical four chamber view of the heart is being displayed. The second zone 304 displays an ECG trace. The third zone 306 displays parameters used by the ultrasound system to form an ultrasound signal, such as the gain (100) and the output MI of the transducer(0.6). The fourth zone 308 is a graph 310 of MI versus depth.

The graph 310 indicates what areas are being submitted to high MI. The individual ultrasound waves output by each element of a transducer are delayed to provide steering and focusing, causing the individual waves to "pile up," e.g. focus, at a predefined location. This predefined location will receive a large portion of the energy from the transducer. By knowing the depth at which the MI is the greatest, sonographers can ensure that any one depth is not submitted to high MI any longer than necessary. This function can also be automated, by, for example providing a control program that issues a warning when the maximum MI has stayed at the same depth for too long. The control program could even be further modified to automatically change the focus depth or power output after a predetermined amount of time.

Preferably, the determination of the MI for any given depth is based on prior experimentation. Perhaps the simplest method is to perform a series of measurements, varying each of the settings that control the output of the transducer, in a lab using a water tank and extrapolate these measurements, using known methods, to a human body. Using the system shown in FIG. 1 as an example, the memory 136 may be loaded with a table correlating MI and depth for each of the various settings. During an examination, the table would be accessed using the settings of the system to retrieve values indicating an estimate of the MI at various depths. Alternatively, simulation software may be used instead of physical water tank testing. Given the computer power present on most current ultrasound systems, such simulation software can be run in parallel with an examination to provide real time simulated values for MI vs. depth.

Figure 4:
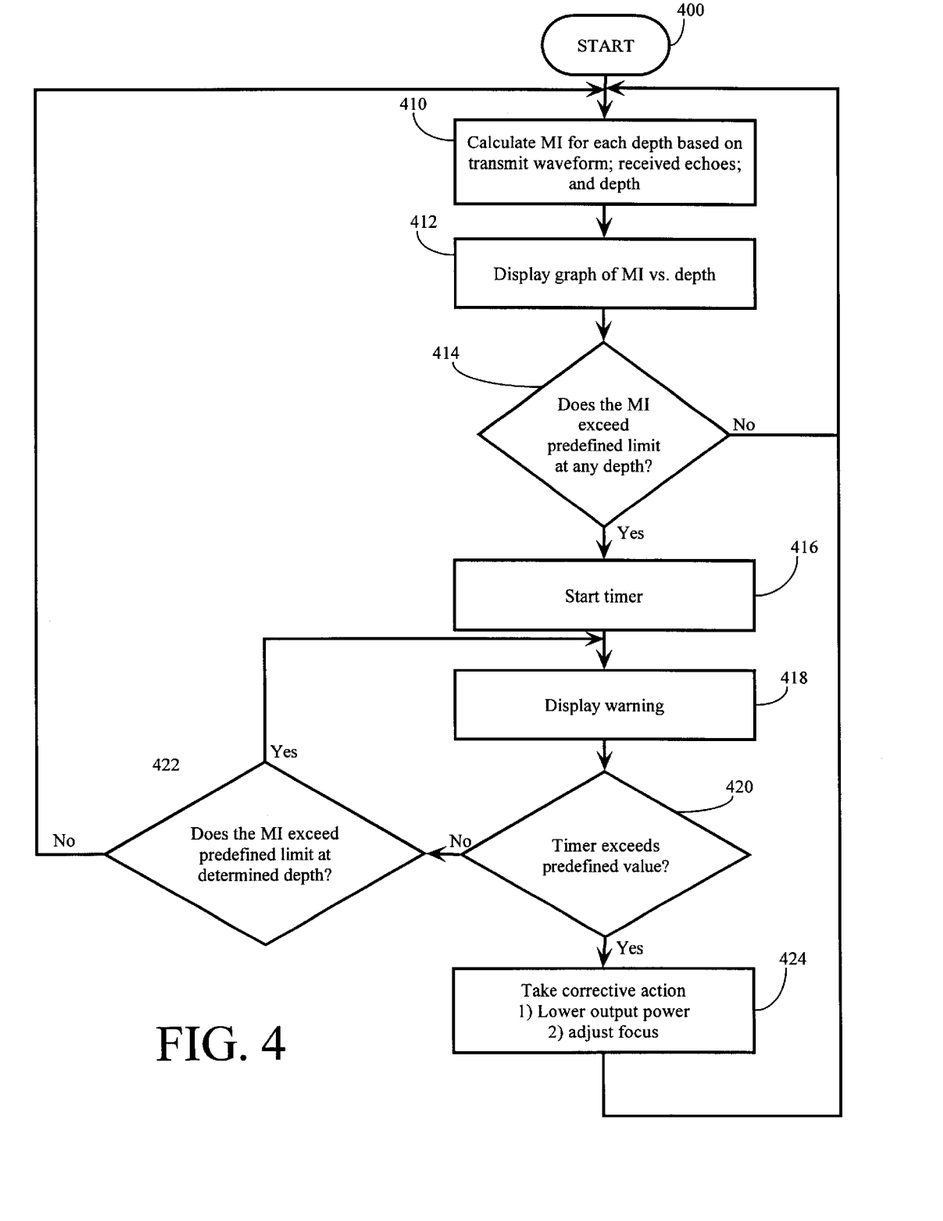
FIG. 4 is a flow chart of a routine in accordance with the first preferred embodiment of the present invention.

FIG. 4 is a flow chart of a routine in accordance with the first preferred embodiment of the present invention. The routine starts in step 400. The MI for each depth (up to the effective depth of the transducer or for a given range around the focus depth) is calculated based on, for example, the current output settings, the received echoes, and the depth. Thereafter in step 412 a graph is created and displayed on a display. Preferably, the display is the same display used for showing the ultrasound images.

In step 414 a check is made as to whether the MI at any depth exceeds a predefined limit, such as 1.9. If the MI at each depth is below the limit, the routine returns to step 410 and the calculation is performed again. Otherwise, in the event that the predefined limit is exceeded, a timer is started in step 416 and a warning is displayed in step 418.

In step 420, a check of the timer is performed. If the timer does not exceed a predefined value a check is made in step 422 as to whether the MI, at the determined depth, still exceeds the predefined limit. If the MI has dropped below the predefined limit, the routine returns to step 410, otherwise, the routine returns to step 418 an repeats steps 418 and 420. If the MI, at the detected depth, continues to remain above the predefined limit for longer than the predefined time, step 424 will be activated by step 420. In step 424, corrective action is implemented. The exact corrective action taken can be defined in advance and may, for example, be 1)lowering the output power to below 1.9 MI or perhaps stopping the output of the transducer all together; 2) changing the imaging mode; 3) softening the focus; and/or 3) adjusting the focus to a different depth. Once the corrective action is taken the routine returns to step 410.

Those of ordinary skill in the art will recognize that further enhancements can be made to the routine shown in FIG. 4. For example, activation of step 424 could trigger a counter that adjusts the corrective action taken. The first time step 424 is activated a warning message could be displayed, requiring operator recognition (such as a WINDOWS message box), the second time the output power could be lowered under 1.9 MI for a predetermined time, and the third time the output power could be lowered to 0.0 MI and the ultrasound system locked until an appropriate password is entered.

Figure 5:
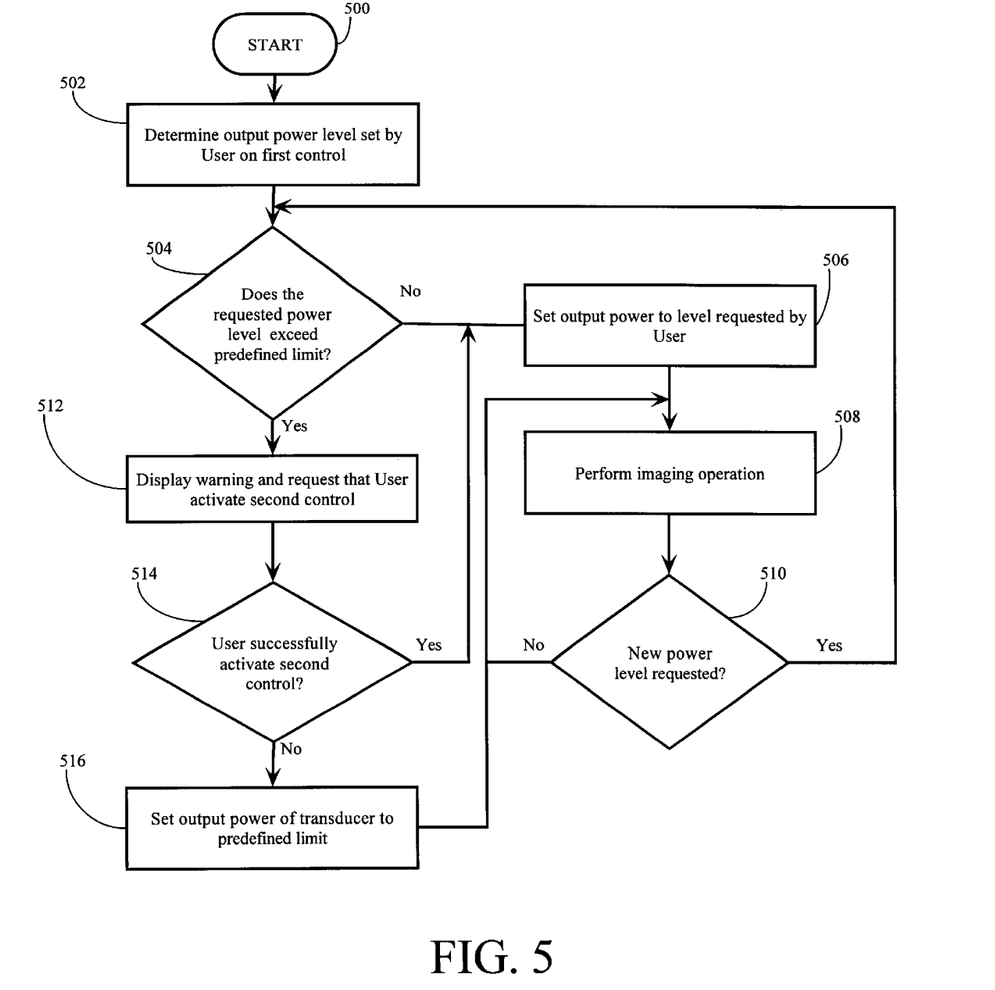
FIG. 5 is a flow chart of a routine in accordance with a second preferred embodiment of the present invention.

FIG. 5 is a flow chart of a routine in accordance with a second preferred embodiment of the present invention. The routine starts in step 500. In step 502 the output power level set by a user, using a first control, is determined. The first control can take a variety of forms, including: a dial, a slider, a menu, or either a hard or soft keyboard.

In step 504, a determination is made as to whether the power level requested by the user exceeds a predefined limit, such as 1.9 MI. If the requested power level does not exceed the limit, the routine goes to step 506 and the output power is set to the level requested by the user in step 502. Subsequently, the imaging operation is performed in step 508. Subsequent checks are made in step 510 as to whether a new power level has been requested. If no new power level is requested the imaging operation simply continues by returning to step 508, other wise, when a new power level is requested a return to step 504 is made.

If in step 504, the requested power level exceeds the predefined limit, the routine goes to step 512 and a warning is displayed. The warning includes a request that the user activate a second control to proceed with the high MI imaging operation. The second control can be any one or combination of controls, including: a dial, a slider, a menu, and either a hard or soft keyboard. In the event of a keyboard control, passwords can be requested and verified allowing the discrimination of user between those authorized to perform high MI scans and those who are not.

In step 514, a check is made as to whether the user successfully activated the second control. If the second control was successfully activated the routine goes to step 506 and the output power is set to the level requested by the user. Otherwise, the routine proceeds to step 516 and the power level is set to a predefined limit, such as 1.9 MI. In either case, once the power level is set, the routine goes to step 508 and the imaging operation is performed.

Those of ordinary skill in the art will recognize that further enhancements can be made to the routine shown in FIG. 5. For example, the amount of time spent above the predefined limit could be monitored and, should the amount of time exceed a certain value, an additional activation of the second (or other) control could be required. Alternatively, the power level could be automatically lowered when the amount of time exceeds the certain value. Additionally, the routine shown in FIG. 5 could be combined with the routine shown in FIG. 4.

Figure 6:
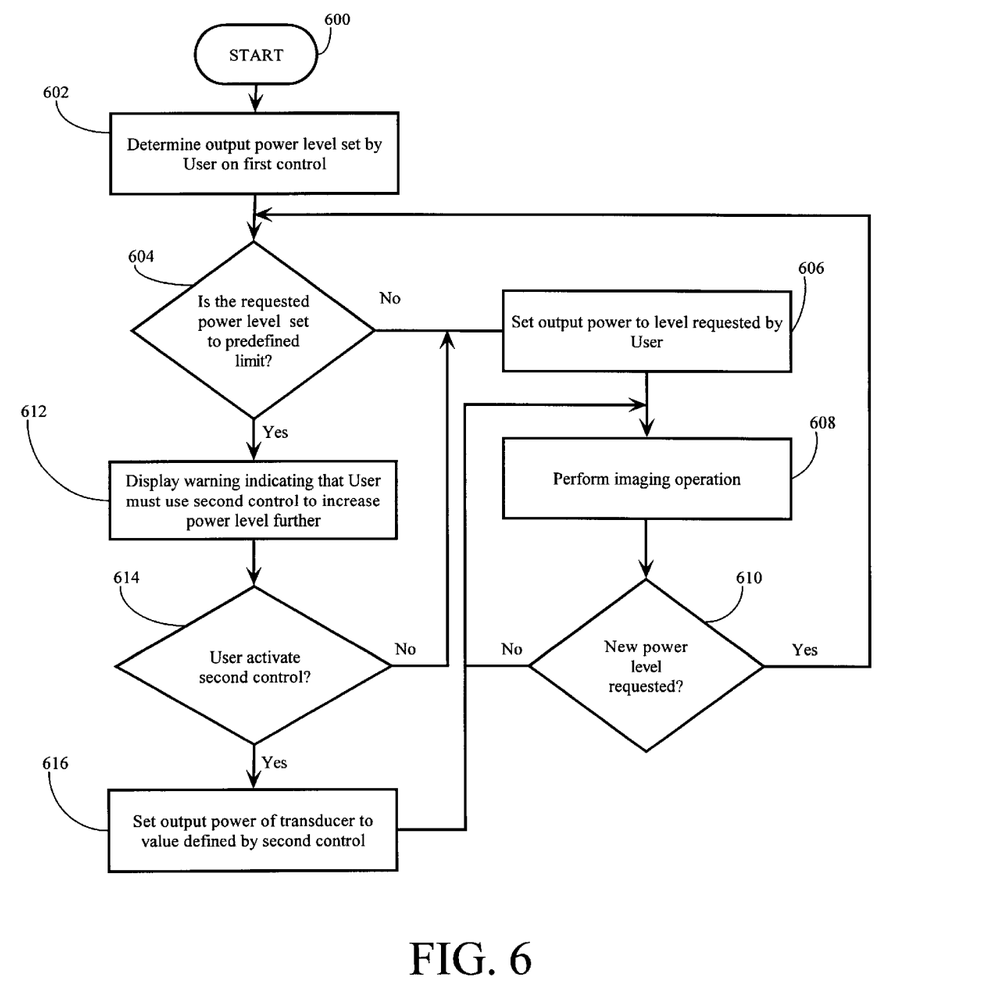
FIG. 6 is a flow chart of a routine in accordance with a third preferred embodiment of the present invention.

FIG. 6 is a flow chart of a routine in accordance with a third preferred embodiment of the present invention. The routine shown in FIG. 6 is a variant of that shown in FIG. 5. Basically, the second control is used to set power level above a predefined value, as opposed to simply confirming the power level as in the routine shown in FIG. 5.

The routine starts in step 600. In step 602 the output power level set by a user, using a first control, is determined. The first control can take a variety of forms, including: a dial, a slider, a menu, and either a hard or soft keyboard.

In step 604, a determination is made as to whether the power level requested by the user is set to a predefined limit, such as 1.9 MI. Typically, the first control will be an analog style control, so this determination is made by simply determining if the control is set to its maximum limit. If the requested power level does not exceed the limit, the output power is set to the level requested by the user in step 606 and the imaging operation is performed in step 608. Subsequent checks are made in step 610 as to whether a new power level has been requested. If no new power level is requested the imaging operation simply continues by returning to step 608, otherwise, when a new power level is requested a return to step 604 is made.

If, in step 604, the requested power level is at the predefined limit, the routine goes to step 612 and a warning is displayed. The warning includes a request that the user utilize a second control to request power levels above the predefined limit. The second control can be any of a variety of controls, including: a dial, a slider, a menu, and either a hard or soft keyboard. Preferably, the control will be one that requires digital input, so as to increase the difficulty of using higher MIs. In the event of a keyboard control, passwords can be requested and verified allowing the discrimination of user between those authorized to perform high MI scans and those who are not.

In step 614, a check is made as to whether the user activated the second control. If the second control was not activated the routine goes to step 606 and the output power is set to the level requested by the user, e.g. the predetermined limit for the first control. Otherwise, the routine proceeds to step 616 and the power level is set to a value defined by the second control. In either case, once the power level is set, the routine goes to step 608 and the imaging operation is performed.

Those of ordinary skill in the art will recognize that further enhancements can be made to the routine shown in FIG. 6. For example, the amount of time spent above the predefined limit could be monitored and, should the amount of time exceed a certain value, an additional activation of the second (or other) control could be required. Alternatively, the power level could be automatically lowered when the amount of time exceeds the certain value. Additionally, the routine shown in FIG. 6 could be combined with the routine shown in FIG. 4.

Figure 7:
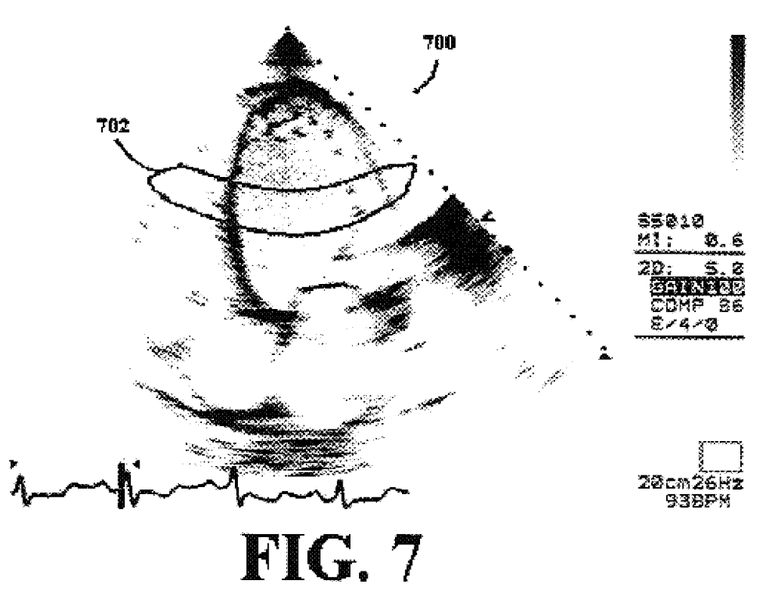
FIG. 7 is a screen shot of an image produced by an ultrasound system in accordance with a fourth preferred embodiment of the present invention.

FIG. 7 is a screen shot of an image produced by an ultrasound system in accordance with a fourth preferred embodiment of the present invention. The image 700 shown in FIG. 7 is similar to that shown in FIG. 3 in that the user is presenting with an indication of where the peak MI occurs. In this case, an area 702 receiving the peak MI is highlighted, using for example, color, shading, or boxing (as is employed in the example shown in FIG. 6.). The area that receives the peak MI can be determined using a table derived from experimental data (similar to the table used to determined MI v. Depth described above) or preferably by using simulator software running in parallel to the examination routine.

In accordance with the foregoing, the present inventors have described methods and apparatus that provide for increased safety when operating ultrasound imaging equipment, and are especially suited for high MI imaging. This represents a significant advance over the prior art which merely limited the output power of a transducer.

Although a few preferred embodiments of the present invention have been shown and described, it would be appreciated by those skilled in the art that changes may be made in these embodiments without departing from the principles and spirit of the invention, the scope of which is defined in the claims and their equivalents. For example, while the preferred embodiments are described with reference to a medical ultrasound imaging system, the present invention is applicable to other ultrasound systems and may, in fact be applicable to other imaging systems.

What is claimed is:

1. An ultrasound imaging device comprising:
   a transducer that outputs an ultrasonic imaging signal;
   a first controller for low MI imaging;
   a second controller for high MI imaging; and
   a control circuit that in response to input from the first controller adjusts the output of the transducer for low MI imaging and when a power level over a predetermined value is input from the first controller, the control circuit requires input from the second controller to adjust the output of the transducer to the requested power level for high MI imaging.

2. An ultrasound imaging device, as set forth in claim 1, wherein the second controller is a mechanical controller.

3. An ultrasound imaging device, as set forth in claim 1, wherein the second controller is a menu.

4. An ultrasound imaging device comprising:
   a transducer that outputs an ultrasonic imaging signal;
   a display device; and
   a control circuit that causes said display to display a graph of MI vs. depth.

5. An ultrasound imaging device, as set forth in claim 4, wherein the control circuit causes said display device to display the graph of MI vs. depth in conjunction with displaying an ultrasound image produced by processing echoes of the ultrasonic imaging signal.

6. An ultrasound imaging device, as set forth in claim 4, wherein the control circuit causes a warning to be displayed if the MI for any depth goes above a predetermined value.

7. An ultrasound imaging device, as set forth in claim 6, wherein the predetermined value is 1.9.

8. An ultrasound imaging device, as set forth in claim 4, wherein the control circuit lowers the power output of the transducer if the MI for any depth goes above a predetermined value for a predetermined time.

9. An ultrasound imaging device, as set forth in claim 8, wherein the predetermined value is 1.9.

10. An ultrasound imaging device comprising:

a transducer that outputs an ultrasonic imaging signal and receives echoes of the ultrasonic imaging signal;

a display device; and a control circuit that causes said display device to display an image based upon the received echoes and highlights portions of the image corresponding to the region being displayed receiving the highest MI, the highlighting including at least one of color, shading and boxing.

11. An ultrasound imaging device, as set forth in claim 10, wherein the portion of the image corresponding to regions receiving MI exceeding a predetermined value are highlighted.

12. An ultrasound imaging device, as set forth in claim 11, wherein the predetermined value is 1.9.

13. An ultrasound imaging device, as set forth in claim 10, wherein the portion of the image corresponding to regions receiving the highest MI are determined based upon an output of a simulator program.

14. An ultrasound imaging device, comprising:

a transducer that outputs an ultrasonic imaging signal and receives echoes of the ultrasonic imaging signal;

a display device; and a control circuit that causes said display device to display an image based upon the received echoes and highlights portions of the image corresponding to the region being displayed receiving the highest MI, wherein the portion of the image corresponding to regions receiving the highest MI are determined based upon a table reflecting the results of prior experiments.

15. An ultrasound imaging device comprising:

a transducer that outputs an ultrasonic imaging signal;

a first controller that receives a value from a user requesting a certain power level to be output by the transducer;

a second controller for confirming high MI imaging; and a control circuit that in response to input from the first controller adjusts the output of the transducer and when the requested power level exceeds a predetermined level, issues a warning to the user and holds the output of the transducer at the predetermined level until the user manipulates the second controller.

16. An ultrasound imaging device, as set forth in claim 15, wherein the predetermined level is 1.9 MI.

17. An ultrasound imaging device comprising:

a transducer that outputs an ultrasonic imaging signal;

a first controller;

a second controller; and a control circuit that in response to input from the first controller adjusts a power level output by the transducer within a predefined range and when a power level over a predetermined value which is greater than the predefined range is input from the first controller, the control circuit requires input from the second controller prior to adjusting the power level output by the transducer outside the predefined range.

* * * * *